(12) United States Patent
Burke et al.

(10) Patent No.: US 9,526,508 B2
(45) Date of Patent: Dec. 27, 2016

(54) SURGICAL BUR WITH PLURAL FLUTES AND A GROOVE, THE GROOVE FORMED IN A SINGLE ONE OF THE FLUTES AND SPACED AWAY FROM THE DISTAL END OF THE BUR

(71) Applicant: Stryker Ireland, Ltd., Kalamazoo, MI (US)

(72) Inventors: Thomas Burke, Claremorris (IE); Matteo Gubellini, Glanmire (IE)

(73) Assignee: STRYKER IRELAND, LTD., Cork (IE)

( * ) Notice: Subject to any disclaimer, the term of this patent is extended or adjusted under 35 U.S.C. 154(b) by 92 days.

(21) Appl. No.: 14/637,489

(22) Filed: Mar. 4, 2015

(65) Prior Publication Data
US 2015/0173776 A1    Jun. 25, 2015

Related U.S. Application Data

(63) Continuation of application No. PCT/EP2013/068502, filed on Sep. 6, 2013.

(60) Provisional application No. 61/698,255, filed on Sep. 7, 2012.

(51) Int. Cl.
*A61B 17/16* (2006.01)
*B23C 5/10* (2006.01)

(52) U.S. Cl.
CPC ....... *A61B 17/1615* (2013.01); *A61B 17/1613* (2013.01); *B23C 5/10* (2013.01); *B23C 5/1009* (2013.01); *A61B 17/162* (2013.01); *A61B 2017/1602* (2013.01); *B23C 2210/0414* (2013.01); *B23C 2210/0492* (2013.01); *B23C 2210/086* (2013.01); *B23C 2210/326* (2013.01); *B23C 2210/486* (2013.01); *B23C 2250/16* (2013.01)

(58) Field of Classification Search
CPC ............ A61B 17/16; A61B 2017/1602; A61B 17/1613; A61B 17/1615; A61B 17/162; B23C 5/10; B23C 5/1009; B23C 2210/0414; B23C 2210/0492; B23C 2210/086; B23C 2210/486
See application file for complete search history.

(56) References Cited

U.S. PATENT DOCUMENTS

| | | | |
|---|---|---|---|
| 4,284,406 A * | 8/1981 | Hughes | ................ A61C 3/02 407/53 |
| 5,888,200 A | 3/1999 | Walen | |
| 6,562,055 B2 | 5/2003 | Walen | |

(Continued)

OTHER PUBLICATIONS

PCT International Search Report and Written Opinion for PCT/EP2013/068502, dated Oct. 2014.

*Primary Examiner* — Larry E Waggle, Jr.

(57) ABSTRACT

A bur with features that minimize the application of substantially identical forces to the tissue against which the bur is applied. One of these features is a single groove located in a single one of the flutes. The groove is formed in the flute so as to be spaced proximally away from the distal end tip of the bur head. Another feature is that, adjacent the distal end tip of the bur head, the clearance surfaces of the flutes extend outwardly different distances from the longitudinal axis through the bur head. Another feature is that the flutes extend in a helical pattern around the bur head and the angle of the helix varies along the longitudinal axis of the bur head.

23 Claims, 4 Drawing Sheets

(56) References Cited

U.S. PATENT DOCUMENTS

| | | |
|---|---|---|
| 2009/0048602 A1 | 2/2009 | O'Donoghue |
| 2010/0063524 A1 | 3/2010 | McCombs |
| 2011/0144649 A1* | 6/2011 | Victor ................ A61B 17/1617 606/80 |
| 2012/0009543 A1* | 1/2012 | Meier ................ A61B 17/1615 433/165 |
| 2012/0150209 A1 | 6/2012 | Gubellini et al. |
| 2012/0158028 A1 | 6/2012 | O'Sullivan et al. |
| 2012/0208147 A1* | 8/2012 | Krumsiek ................ A61C 3/02 433/144 |

* cited by examiner

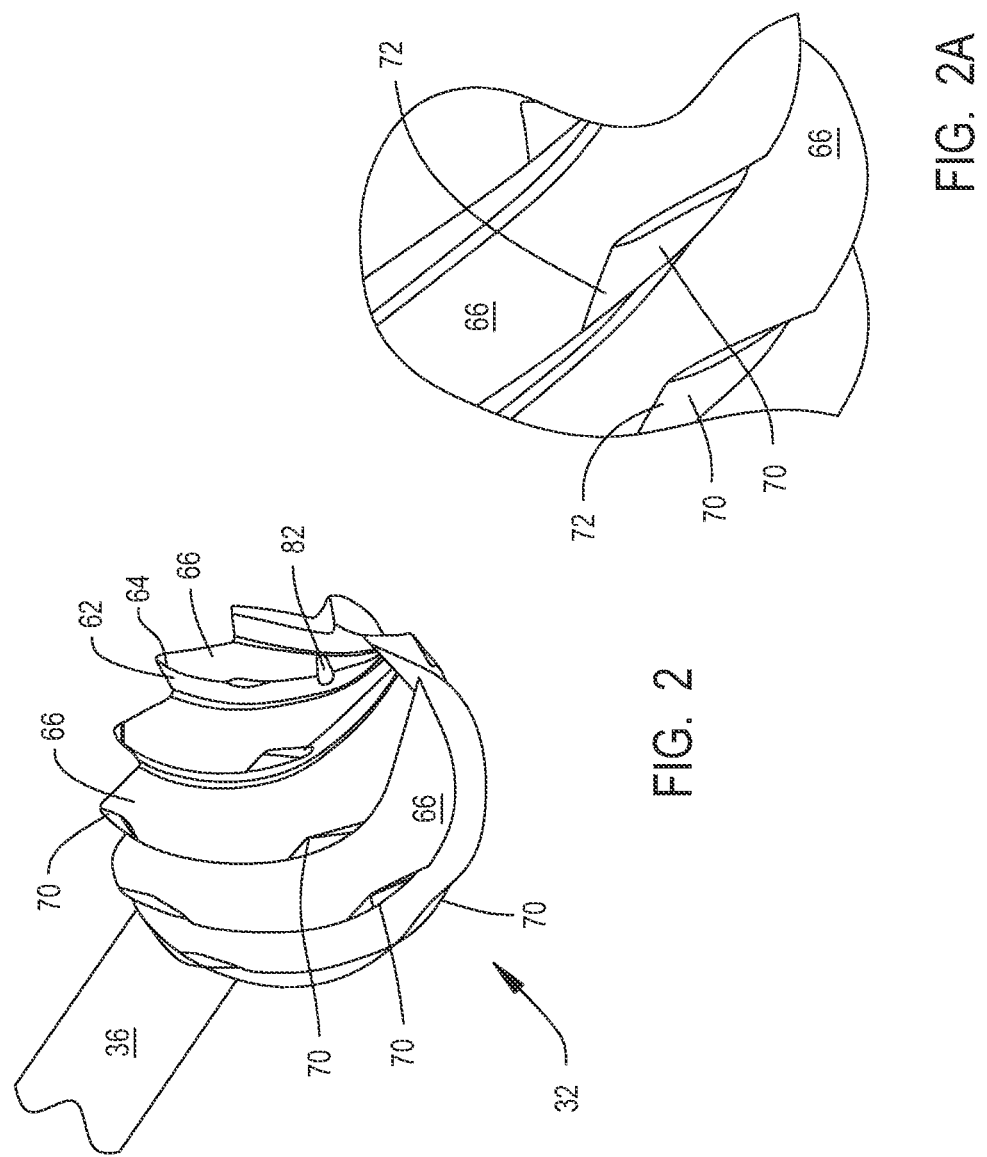

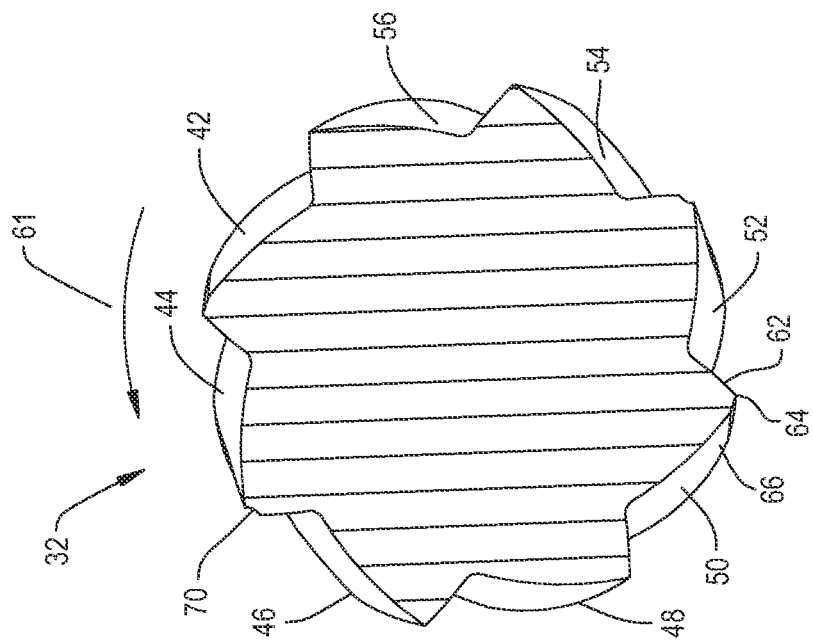
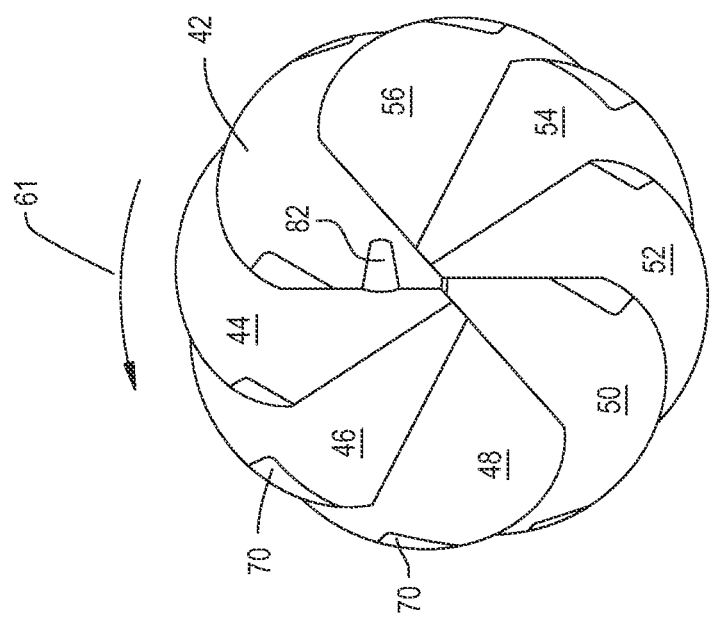
FIG. 4
FIG. 3

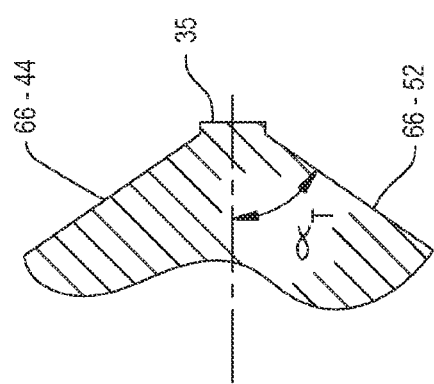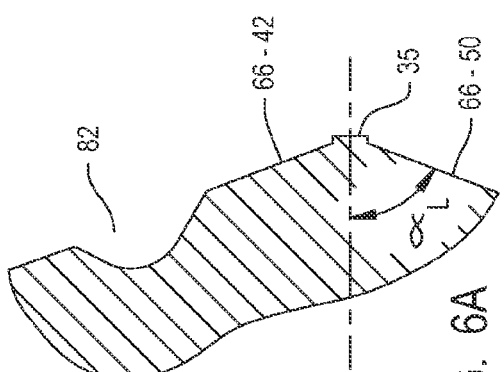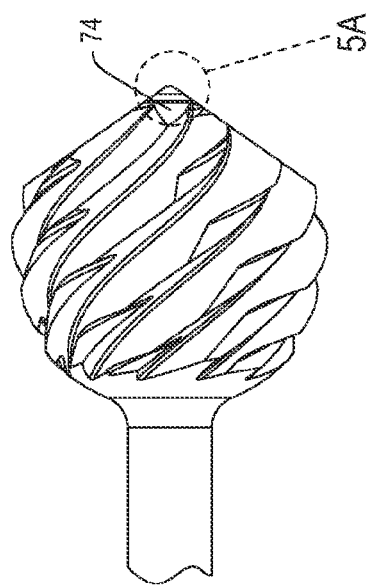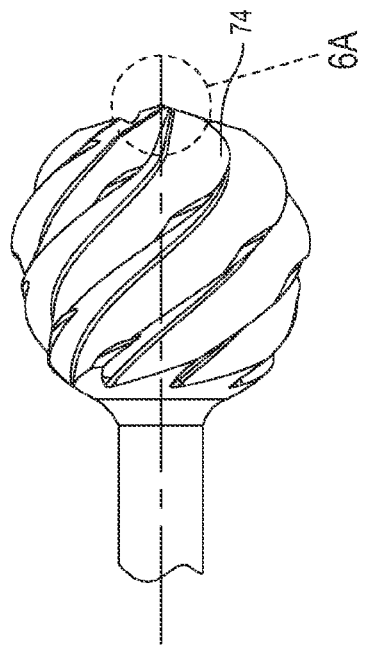
FIG. 5A
FIG. 6A
FIG. 5
FIG. 6

SURGICAL BUR WITH PLURAL FLUTES AND A GROOVE, THE GROOVE FORMED IN A SINGLE ONE OF THE FLUTES AND SPACED AWAY FROM THE DISTAL END OF THE BUR

RELATIONSHIP TO EARLIER FILED APPLICATIONS

This application is a continuation of PCT App. No. PCT/EP2013/068502 filed 6 Sep. 2013. PCT App. No. PCT/EP2013/068502 claims the benefit of U.S. Prov. Pat. App. No. 61/698,255 filed 7 Sep. 2012. The contents of the above-listed priority applications are incorporated herein by reference.

FIELD OF THE INVENTION

This invention is generally related to surgical burs. More particularly, this invention is related to a surgical bur with flutes that are both non-uniform in shape and that have varying inter-flute separations to reduce chatter when the bur is applied to a surgical site.

BACKGROUND OF THE INVENTION

One cutting accessory used to perform a surgical procedure is the bur. A bur generally consists of a head formed from rigid material, typically metal, shaped to have a number of flutes. The flutes are formed to define cutting edges. More particularly, the flutes are typically designed to cut hard tissue, such as bone or cartilage. A shaft extends rearwardly from the head. The proximal end of the shaft often has a feature that facilitates locking the shaft to a powered handpiece. The actuation of the handpiece results in the rotation of the bur. During a surgical procedure, the bur head is placed against a surgical site where a section of tissue is to be removed. The rotating cutting edges excise tissue away from the surgical site. Burs of various shapes and sizes are used in procedures such as orthopedic surgery, neuro and spinal surgery, ear noise and throat surgery and in other surgical procedures in which a sub-procedure is to selectively remove a section of tissue.

Burs work well for the purposes for which they are designed. Nevertheless, a problem associated with some burs is chatter. Chatter is the back and forth vibration of a bur head against the surface to which the bur head is applied. Chatter occurs as a result of bur's individual cutting edges repeatedly being forced against the tissue against which the bur head is applied.

In order to minimize chatter, burs have been proposed with different shaped as well as burs with different spacing between the flutes. The Inventors' Assignee's US Pat. Pubs. No. 2009/0048602 published 19 Feb. 2009, No. US 2012/0150209 published 13 Jun. 2012 and No. US 2012/0158028 published 21 Jun. 2012 disclose burs having flutes shaped and arranged to minimize bur vibration. Each of these publications is understood to be incorporated into reference into this application.

The above burs do have features that in some situations do serve to minimize bur vibration. Still there are some applications in which many burs when applied to soft or hard tissue, may still appreciably vibrate.

Also, there may be some procedures in which the surgeon using the bur may want to apply the bur in a backwards manner against the tissue the bur is being employed to remove. Here "backwards" is understood to mean that instead of applying a force that moves the bur away from the practitioner or sideways, laterally relative to the longitudinal axis of the bur, the surgeon draws the bur back towards himself/herself. This type of manipulation is employed if the tissue to be removed is difficult to remove by the mere pressing of the bur in the forward direction or sideways. A problem using some burs to perform this type of procedure is that their flutes do not extend a significant distance proximally behind their equators, the plane of bur maximum diameter. Many known burs, for example, have flutes that, proximally from the equator, terminate at a circle that has a diameter approximately equal to one-half of the diameter of the bur itself. This means that proximal to this circle, the bur is fluteless. Consequently, the pressing of this proximal portion of the bur head against tissue does not serve to remove any of the tissue to which this section of the bur is applied.

Thus, sometimes in order to backwards move the fluted proximal portion of the bur head against the tissue to be removed, the surgeon invariably has to press the fluteless section of the bur head against tissue that does need removal. The rubbing of this fluteless section of the bur head against the tissue frictionally heats this tissue. There may be situations in which this frictional heating results in the thermal necrosis of tissue that ideally should not be affected by the procedure for which the bur is employed.

There have been efforts to provide burs with flutes that extend proximally back closer to the shaft from which the bur head extends. This has resulted in burs that, in a single rotation, remove more tissue than the surgeon wants to remove. This type of bur is sometimes referred to as an overly aggressive bur. Further these burs have a tendency to vibrate to the extent that the vibrations adversely affect the ability of the surgeon to control, to position, these burs.

SUMMARY OF THE INVENTION

This invention is directed to a new and useful surgical bur. The bur of this invention includes flutes shaped to minimize the vibration of the bur head to which the flutes are integral.

One feature of the bur of this invention is that the flutes are arranged in a helical pattern around the head from which the flutes project. More particularly, the flutes are shaped so that each flute extends around the head in a helix that has a varying helix angle as well as rake surface that has varying rake angle. Both the helix angle and rake angle vary along the length of the head from which the flutes extend radially outwardly. In many versions of the invention, proximal to the mid-point of the bur the rake angle of the flutes decrease.

A further feature of the bur of this invention is that that at least some if not all of the flutes are formed with a cross cut. In many versions of the invention the cross cut has a base surface that has a negative rake angle. In some versions of the invention one or more of the flutes are formed with plural cross cuts.

A further feature of this invention, that at least one flute is formed with a groove so as to function as a chip breaker. More particularly, the one or more chip breaking grooves are arranged asymmetrically relative to the distal end tip of the bur head.

A further feature of this invention is that the cross cuts are arranged so that cross cuts on the angularly adjacent flutes are spaced apart from each other along the longitudinal axis of the bur head.

It is still an additional feature of the bur of this invention that owing to the shaping of the flutes, the distal end tip of the bur head, as it rotates appears to define an angle that as the bur head rotates through a fixed plane, varies.

A bur of this invention may be constructed to have one, two or more or all of the above features.

BRIEF DESCRIPTION OF THE DRAWINGS

The invention is pointed out with particularity in the claims. The above and further features of this invention may be better understood by reference to the following detailed description taken in conjunction with the accompanying drawings in which:

FIG. 2 is a perspective view of the head of the bur of this invention

FIG. 2A is an enlarged perspective view of a cutouts formed in the flutes of FIG. 2;

FIG. 3 is a front plan view of the bur head;

FIG. 4 is a cross sectional view of the bur head in the plane perpendicular to the longitudinal axis through the bur head;

FIG. 5 is an enlarged side view of the bur head;

FIG. 5A is a cross sectional view of the tip of the bur of FIG. 5, the view being in the plane of the page of FIG. 5;

FIG. 6 is an enlarged side view of the bur head, the bur head being rotated 90° around the longitudinal axis from the orientation depicted in FIG. 5; and FIG. 6A is a cross sectional view of the tip of the bur of FIG. 6, the view being in the plane of the page of FIG. 6;

DETAILED DESCRIPTION

Figure 1:
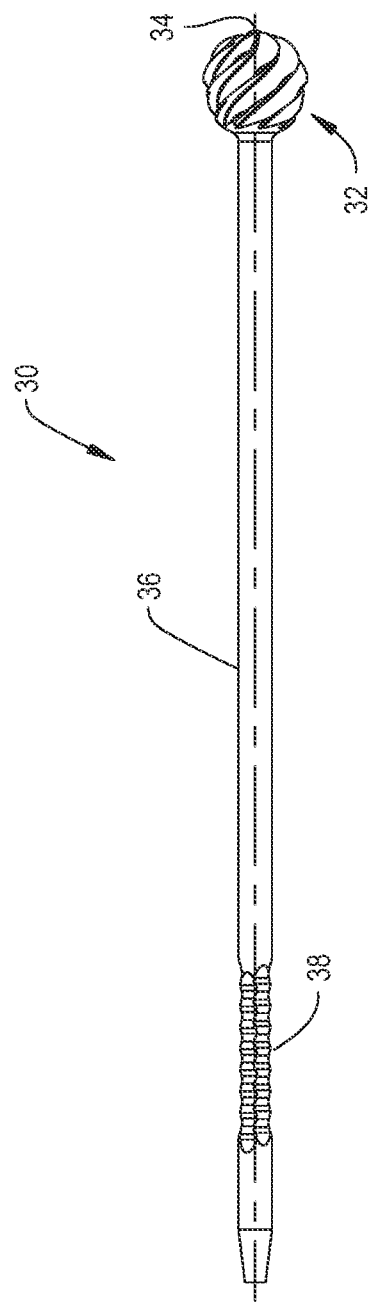
FIG. 1 is a side view of surgical bur constructed according to this invention.

FIG. 1 illustrates a surgical bur 30 constructed in accordance with this invention. Bur 30 has a head 32 that forms the distal end of the bur. ("Distal" it is understood, means towards the surgical site to which the bur is applied. "Proximal" means away from the surgical site.) Bur head 32 has a distal end tip 34 that is the most forward portion of the bur 30. A shaft 36 extends proximally rearward from the bur head 32. Not identified is the tapered neck that extends between the shaft 30 and head 32. This neck is tapered in that extending distally from the shaft, the outer diameter of the neck increases.

In many versions of this invention, bur 30 is designed to perform neurological, ENT, spinal or orthopedic surgical procedures. Accordingly, in many versions of the invention bur head 32 has a maximum outer circumference of 15 mm or less. In other versions of the invention, the maximum outer circumference of the bur head 32 is 10 mm or less.

The proximal end of the shaft 36 is provided with coupling features 38. The coupling features 38 are geometric features that facilitate the removable engagement of the shaft 36 to a coupling assembly integral with the rotating shaft of a powered surgical handpiece with which bur 30 is used (handpiece not illustrated.) This handpiece is sometimes called a drill or tool. The illustrated coupling features 38 are concave faces recessed relative to the outer diameter of the shaft 36. The pattern of the arrangement of these faces is discussed in US Pat. Pub. No. 2010/0635524, published 11 Mar. 2010 the contents of which are incorporated herein by reference. Alternative geometries and arrangements of retention features are described and illustrated in U.S. Pat. No. 5,888,200, issued 30 Mar. 1999, and U.S. Pat. No. 6,562,055, issued 13 May 2003, both of which are incorporated herein by reference. It should be appreciated that these geometries of coupling features are exemplary, not limiting.

In alternative versions of the invention, these coupling features may for example, be threading. Alternatively, tabs that project outwardly from the outer surface of shaft 36 may function as the coupling features. In some versions of the invention, the coupling feature 38 may simply be a section of the smooth walled shaft 34 against which the fingers of a tool chuck bear to hold the bur 30 to the tool. Thus, the exact geometry of the coupling feature is not relevant to the structure of this invention.

A number of arcuately spaced apart flutes 42-56 extend radially outwardly from the center of bur head 32 as seen best in FIGS. 2 and 3. Each flute 42-56 is shaped to have a rake surface 62 and a clearance surface 66, one of each identified in FIG. 4. In the direction in which the bur head and flutes rotate, arrow 61 of FIG. 4, the rake surface 62 is the leading surface; the clearance surface 66 is the surface of the flute that follows the rake surface 62. The edge along which the rake surface 62 and clearance surface 66 of a flute meet is the cutting edge 64 of the flute.

Surgical bur 30 of this invention is formed so that the flutes have a helical shape. Specifically this means that as a flute 42-56, extends proximally extends proximally away from tip 34, the rake surface and clearance surface are shaped so that as the cutting edge 64 extends longitudinally, the cutting edge curves around the outer surface of the bur head 32. More particularly, bur 30 is designed so that helix angle of a flute cutting edge 64 varies along the length of the flute. The helix angle of the cutting edge 64, it is understood is the acute angle of segment of the cutting edge relative to the longitudinal axis of the bur. The bur longitudinal axis is the axis that extends from the distal end tip 34 to the proximal end of the bur head 32. Adjacent the distal end tip of each flute 42-56 the helix angle is essentially 0°. Extending distally from tip 34 the helix angle increases. In one version of the invention, the helix angle increases to a maximum of between 45 and 65° and more often between 50 and 60°. The helix angle of the flute is it a maximum adjacent the equator of the bur head 32. This equator is understood to be the plane perpendicular to the longitudinal axis of the bur head where the bur head diameter is at a maximum. Bur 30 of this invention is further formed so that, proximal to the equator, the helix angle of the flutes 42-56 decrease. In some versions of the invention, this decrease is between 5 and 30° relative to the largest helix angle.

In still other versions of the invention this decrease is between 10 and 20° relative to the largest helix angle.

Each flute also has a rake angle. The rake angle is the angle of the rake surface 32 relative to a radial line that extends from the longitudinal axis of the bur head to the cutting edge of the flute. This line is understood is located in plane perpendicular to the longitudinal axis of the bur head 32. Bur 30 of this invention is further formed so that the rake angle varies along the length of the flutes 42-56 varies along the length of the flutes. More particularly, in many versions of the invention the rake angle becomes more negative as the flute extends proximally away from tip 34. (The rake angle is "neutral,") (0° if the rake surface is in line with the radial line from the longitudinal axis of the bur head. The rake angle is "negative") (<0° if the rake surface extends forward from the radial line from the longitudinal axis of the bur head. The rake angle is "positive") (>0° if the rake surface extends rearward from the radial line from the longitudinal axis of the bur head.) In some versions of the invention, the bur is formed so that adjacent the distal end tip 34 the rake angle is between −10° and 10° and more particularly between−5° and 5°. The rake angle decreases so that adjacent the proximal end of the bur head the rake angle is between −70° and −20° and more often between −56° and −40°.

In some methods of forming bur 30 of this invention, a workpiece is formed so as to have the shape of a shaft 36 with a head. This head, for the described bur, would be substantially spherical in shape. The diameter of this head would be at least as large as the diameter of the finished bur head 32. A grinding wheel is then brought down against the bur head. Often this grinding wheel is brought down against the equator of the head of this workpiece.

The grinding wheel, which is rotating, is moved in a helical path against the head of the workpiece. The grinding wheel thus forms the clearance surface 66 of a first flute as well as the rake surface of the flute adjacent the flute for which the clearance surface is being formed.

It should further be understood that as the grinding wheel is moved along the surface of the head of the workplace, the position of the wheel relative to the center of this head is varied. More particularly, adjacent the equator of the head, the grinding wheel is closest to the center of this head of the workplace. Both proximal and distal to this equator, the distance between the surface of the grinding wheel and the center of the head of the workpiece is decreased. Thus, it is a further feature of some versions of this invention that flute depth, the radial height of the rake surfaces 62 are at a maximum at the equator of the bur head. The height of the rake surfaces, the depth of the flutes, decreases as the flutes extend proximally and distally to the plane that extends through this equator.

Bur 30 is further formed so that each flute 42-56 typically has at least one cross cut 70. A cross cut 70 is a gap in the flute that separates the cutting edge 64 into different sections. More particularly, a grinding wheel is applied to each flute to form a face 72 that extends from the flute rake surface 62 to the clearance surface 66. The face 72 extend from rake surface so as to extend both inwardly, toward the longitudinal axis of the bur head and arcuately, toward the next flute that, in the order of rotation of the bur head, would strike the tissue to which the bur is applied. This face 72 defines the base of the cross cut 70.

In many versions of the invention, the bur head is formed with flutes 42-56 initially extends as uninterrupted features along the bur head 32. Once the flutes are formed a grinding wheel is applied across each flute to form the individual faces 72. More particularly, this grinding wheel is moved across each flute in a helical path. The curve of this helix is opposite in direction to the curve of the section of the flute 42-56 in which the face is being formed. Consequently, extending arcuately away from the section of the rake surface 62 from which a face 72 extends, the face 72 curves away from the rake surface both towards the rake surface of the arcuately adjacent flute and inwardly so as to curve radially inwardly from the cutting edge 64 of the flute in which the face is formed. In the illustrated version of the invention, the flutes are more specifically formed so that each flute has two cross cuts 70.

Further, bur 30 of this invention is formed so that closest cross cuts of two flutes 42-56 that are arcuately adjacent each other are not centered on the same cross sectional plane that intersects the longitudinal axis through bur head 32. Thus as seen in FIG. 3, the distalmost cross cut 70 formed in flute 46 is spaced distally forward of the distalmost cross cut 70 formed in the arcuately adjacent flute 48. Also in versions of the invention provided with an even number of flutes, the cross cut formed in one flute is formed in the flute the same distance from distal end tip 34 that the cross cut is formed in the diametrically opposed flute. Thus, the distalmost cross cut formed in flute 44 is located the same distance from distal end tip 34 as the distalmost cross cut formed in the opposed flute, flute 52.

Bur 30 is further designed so that the distal ends of two symmetric flutes, here flutes 42 and 50, are the flutes that start at a location along the longitudinal axis of the bur head that is closest to the tip 34. More particularly, as seen in FIG. 6A, the clearance surfaces 66-42 and 66-50 of, respectively, flutes 42 and 50 are each angled a first acute angle, angle $\alpha_L$, to the longitudinal axis of the bur head 32. It is further observed that clearance surfaces 66-42 and 66-50 do not meet to form an edge. Instead these surfaces are spaced apart from each other. Between clearance surfaces 66-42 and 66-50 the bur head thus has a rectangular protrusion called a centering 35. The distal most face of centering 35 is the distal end tip 34 of bur head 32.

The remaining flutes, flutes 44, 46, 48, 52, 54 and 56, are formed to have clearance surfaces that essentially taper away from clearance surfaces 66-42 and 55-50. More specifically, the clearance surfaces of flutes 44, 46 and 48 taper away from clearance surface 66-50. The clearance surfaces of flutes 52, 54 and 56 taper away from clearance surface 66-42. The clearance surfaces of flutes 44, 46, 48, 52, 54 and 56 thus are located along acute angles relative to the longitudinal axis of the bur head that are less than the angles along which the clearance surfaces 66-42 and 66-52. By way of example, FIG. 5A depicts clearance surfaces 66-44 and 66-52, the clearance surfaces associated with, respectively, flutes 44 and 52. Each clearance surface 66-44 and 66-52 is oriented along an acute an acute angle $\alpha_T$ relative to the longitudinal axis through the bur head. Angle $\alpha_T$ is less than angle $\alpha_L$.

As mentioned above, to form the bur of this invention, the head of a workpiece is grinded to form the flutes 42-56. To form the flutes so that flutes 42 and 50 are located on an angle $\alpha_L$ that is greater than the angle $\alpha_T$ of the arcuately leading adjacent flute it may be necessary to form the arcuately leading adjacent flute so that that flute at the widest location, projections radially outward of the adjacent flutes. Here the "arcuately leading adjacent" flute is understood to be the flute that, when the bur head is rotated, strikes tissue immediately before the subject tissue strikes tissue. This flute 44 arcuate leads flute 42. Flute 52 arcuately leads flute 50.

As a consequence of having to so form the bur head as described above, the outer radial portions of flutes 44 and 52 project radially slightly outwardly of the surrounding flutes for flute 44, flutes 42 and 46 and, for flute 52, flutes 50 and 54. As a result, along the equator, bur head has a shape in cross section, that rather than being circular is elliptical. In extreme designs of this invention, this shape can approach an oval.

Another feature of bur 30 of this invention is that at least one of the flutes 42 is formed with a groove 82. In the illustrated version of the invention, only flute 42 is formed with a groove 82. Each groove 82 extends perpendicular to the proximal-to-distal longitudinal axis along the face. The flute/flutes in which the grooves 82 are formed are formed so that longitudinal axis along the groove 82 is between 80 and 100° of the cutting edge 64 of the flute. Cross cuts 70 may not have this relationship with the associated flute cutting edges. It should be understood that in versions of the invention in which both cross cuts 70 and grooves 82 are present, the grooves 82 are located closer to the bur head tip 34 than the cross cuts 70. Further, when the one or more grooves 82 are present, the grooves are located between the bur head tip and the equator of the body of the bur head.

In versions of the invention in which at least one groove 82 is present, the groove/grooves is/are asymmetrically located around the longitudinal axis of the bur head. Thus, if a single groove 82 is present as is depicted in the present drawings, the groove is inherently asymmetrically positioned on the bur head. If plural grooves are present, then the grooves in addition to not being symmetrically located around the bur head longitudinal axis are not equiangularly spaced apart from each.

In some versions of the invention, only a single groove is formed in the bur head. In versions of the invention wherein plural grooves 82 are present the grooves are located different distances distal to tip 32.

Bur 30 of this invention is readied for use by attaching the bur to a handpiece. A coupling assembly integral with the handpiece has features that engage the bur retention features 38. As a result of this engagement, the bur 30 is held to the handpiece so that the bur shaft 36 will rotate in unison with an output shaft connected to the motor internal to the handpiece. Thus, when the handpiece motor is actuated, bur shaft 36, and by extension the whole of bur 30, rotates in unison with the output shaft of the handpiece.

Bur 30 is applied against tissue, typically hard tissue such as bone, to selectively remove the tissue. When the side of the bur head 32 is pressed against tissue to remove the tissue, the flutes 42-56 are sequentially rotated against the tissue. More particularly, each rake surface 62 and cutting edge is pressed against tissue. Owing to each flute being in the shape of varying helix angle helix and having a rake surface 62 that varies in rake angle along the length of the flute, along the length of the interface between the rake surface and the tissue against which this surface and complementary cutting edge 64 are applied, the forces applied to the tissue vary. The varying of these forces reduced the build-up of regenerative forces that are applied to the tissue. By reducing the output of these regenerative forces applied to the tissue, the resultant outputting of reactive forces that the tissue, the bone applies to the bur head is likewise reduced. The reduction of these reactive forces reduces the extent to which the bur head of this invention starts to chatter, vibrate back and forth.

Also, the grinding process used to form the variable helix angle-and-variable rake angle flutes makes it possible to form the flutes 42-56 so that proximal ends of the flutes terminate very close to neck from which the bur head extends. Consequently at the proximal end of the bur, the flute free section of the bur is relatively small in radial width. Here the "radial width" is understood to be length across this section of the bur head starting from where the bur head emerges from the adjacent shaft or neck to the most where the flutes 42-56 start emerging outwardly from the bur head 32. In many versions of the invention the flute free annular section of the bur head 32 immediately adjacent the shaft 36 or neck has a radial width that is less than 25% of the maximum diameter of the bur. More often the radial width of this flute free annular section of the bur head is 20% or less of the maximum diameter of the bur head. In versions of the invention wherein there is a significant likelihood that the bur 30 may be used for back cutting, this flute free annular section of the bur head may have a radial width that is a maximum of 17% of the maximum diameter of the bur head.

An advantage of this feature of the invention is that when a surgeon using the bur 30 of this invention, applies the bur in a backwards motion, substantially all of the proximal section of the bur pressed against the tissue is formed with flutes. This means that when the surgeon applies the bur in this back motion the bur head is can be positioned to essentially only be pressed against tissue the bur is intended to remove. This reduces the extent to which the process in which the bur is employed results in the unintended thermal necrosis of tissue that should not be affected by the process in which the bur is employed.

While the proximal section of the bur of this invention is substantially fluted, owing to the flutes 42-56 having the above discussed helix angles and rake angles in the distal section, the section forward of the equator, the bur when pressed forward or sideways against tissue does not overly aggressively remove tissue or excessively vibrate.

Further, owing to the presence of the cross cuts 70 the cutting force, sometimes referred to as the sheering force, a single flute 42-56 applies the tissue is not applied to the tissue along the length of the flute. This reduces the total amount of cutting force the flute applies to the tissue and, by extension the reactive force the tissue returns back to the flute. The reduction of these forces further reduces the extent to which the bur is induced to chatter.

As mentioned above, another feature of this invention, is that, owing to the flutes extends different radial distances outwardly from the longitudinal axis of the bur 30, the bur head 32 has a shape that appears more elliptical or oval than circular. This feature of the invention likewise causes the forces applied to the tissue to vary. For the reasons set forth above, the varying of these forces over time reduces the generation of reactive forces that induce bur head chatter.

Further there may be some instances when the bur head 32 is applied to the tissue the bur is intended to remove such that the acute angle between the longitudinal axis of the bur head and the plane of the tissue is between 30° through 90°. In these situations the most distal portions of the bur head, the portions of the bur head distal to the equator of the bur head, are applied to the tissue. In these uses of the bur head the sections of the flutes 42-56 in which the one or more grooves 82 are formed are rotated against the tissue. The asymmetric arrangement of these one or more grooves likewise reduces the application of very similar forces against the tissue. This, in turn, results in a like reduction in the build up of reflective forces that induce chatter.

When the acute angle of the bur head 32 and the plane of the tissue is less than 60° and more typically less than 30°, essentially the side portions of the flutes 42-56 are the sections of the flutes that come into contact with the tissue. These are also the sections of the flutes that come into contact when the bur head longitudinal axis is parallel to the plane of the tissue (essentially a 0° angle.) When the bur is so used, as described it is the sections of the flutes 42-56 in which the cross cuts 70, as described above, are rotated against the tissue.

There may likewise be situations in which bur 30 of this invention, is applied to the tissue so as to essentially function as bore forming drill bit. When the bur is so applied to the tissue, the longitudinal axis between the bur and the plane of the tissue is approximately between 60 and 90°. When this occurs a particular plane of tissue against which the bur is applied is, at first moment in time, exposed to cutting edges 64 that are spaced at an angle $2\alpha_L$ apart from each other. At this time, the tissue is exposed to a first force. Immediately after this event, the same portion of tissue is exposed to cutting edges that are spaced apart an angle $2\alpha_T$ apart from each other. At this time the tissue is exposed to a second force that is different from the first force. Thus, the tissue's is exposure to variable forces. Since these forces are variable, instead of being substantially identical, the extent to which the application of these forces induces the generation of chatter inducing reactive forces is reduced.

It should be understood that the foregoing is directed to one specific version of the bur of this invention. Alternative burs constructed according to this invention are possible.

For example, not all burs of this invention may not have all of the features. Thus a bur of this invention may not include: the flutes formed with varying helix angles; the flutes formed with rake angle that varies along the lengths of the rake surfaces; the cross cuts formed to provide the bur head with a shape that, in cross section is elliptical; the asymmetrical located distal end grooves, the tip with a profile that, is not constant around the whole of the circumference of the bur head.

The disclosed version of the invention includes a bur head with eight (8) flutes. This is understood also to be exemplary and not limiting. Thus, at a minimum to have at least some features of this invention a bur head may only have two (2) flutes. For the bur to have additional features of the invention the bur head while often have more than two flutes. Likewise there is no requirement that the bur of this invention always be provided with an even number of flutes. Some burs of this invention may have nine (9) or more flutes.

In the disclosed version of the invention, the groove 82 extends substantially the whole of the width of the flute 42 in which the groove is formed. This is exemplary, not limiting. In some versions of the invention, the groove may on extend from rake surface and terminate before reaching the complementary clearance surface. Likewise, this application should not be interpreted as limiting the depth of either the cross cuts 70 or the grooves 82. In some versions of the invention one or both of the cross cut or one more flutes may have depth that is equal to essentially the complete height of the flute in which this void is formed. Further, in some versions of the invention the groove 82 may be different distances from the bur head tip. Likewise, in some alternative constructions of this invention, a single flute may be formed with plural grooves. A flute of this invention may also have, proximal to the grooves one or more cross cuts.

Further there is no requirement that in all versions of the invention each flute be provided with a cross cut. Also, when cross cuts are formed in the flutes, that each flute have two cross cuts. Some flutes may have a single cross cut and other flutes three or more cross cuts.

Likewise there is no requirement that a bur of this invention always be formed with a head that is generally spherical in shape. In alternative embodiments, the head 32 may have alternative shapes including acorn head, barrel head, bullet head, egg, pear or drum shaped.

Accordingly, it is an object of the appended claims to cover all such variations and modifications that cover the true spirit and scope of this invention.

What is claimed is:

1. A bur for surgical/medical use, said bur including:
   a shaft having opposed proximal and distal ends, said shaft having a proximal section adjacent the proximal end shaped for coupling to a surgical handpiece capable of rotating said shaft; and
   a head attached to the distal end of said shaft, said head having: a tip that is a distal end of said head; a longitudinal axis that extends proximally from the tip through said bur head; and a plurality of flutes, each said flute having a rake surface and a clearance surface, the rake surface and clearance surface meeting at a cutting edge, wherein a single one and only one of said flutes of said plurality of flutes is formed with a groove that extends from the rake surface to the clearance surface, wherein the groove is spaced proximally from the tip of said head so as to separate the cutting edge of said flute in which the groove is formed into a distal section located distal to the groove and a proximal section located proximal from the groove.

2. The bur head of claim 1, wherein said bur head is further formed to have:
   a first set of a plurality of flutes with clearance surfaces that, adjacent the bur head tip, are located a first acute angle relative to the longitudinal axis of said bur head; and
   a second set of a plurality of flutes wherein there is at least one flute from the second set of flutes located between each pair of arcuately adjacent flutes from the first set of flutes, wherein the flutes forming the second set of flutes are formed with clearance surfaces that, adjacent the bur head tip, are located a second acute angle relative to the longitudinal axis of said bur head, the second acute angle being less than the first acute angle so that, in a common plane perpendicular to the longitudinal axis of the bur head, the cutting edges of the flutes of the first set of flutes project radially outwardly from the cutting edge of the flutes of the second set of flutes.

3. The bur of claim 2, wherein said flute formed with the groove is one of the flutes forming the first set of flutes.

4. The bur of claim 2, wherein:
   said bur head is further formed so that the first set of flutes includes two said flutes and said flutes forming the first set of flutes are symmetric to each other relative to the bur head tip; and
   said flute formed with the groove is one of the flutes forming the first set of flutes.

5. The bur head of claim 2, wherein said bur head is further formed so that:
   a plurality of flutes of the second set of flutes are located between each pair of arcuately adjacent flutes of the first set of flutes; and
   said flute formed with the groove is one of the flutes forming the first set of flutes.

6. The bur of claim 1, wherein the groove is formed in said flute so as to have a longitudinal axis that is at an angle of between 80° and 100° of the portion of the flute cutting edge interrupted by the groove.

7. The bur of claim 1, wherein at least one said flute is formed to have a cross cut that extends across said flute, the cross cut being located along said bur head so as to be located proximal to the groove formed in the single said flute.

8. The bur of claim 1, wherein a plurality of said flutes, including the single said flute formed with the groove, are formed so as to each have a cross cut and said flutes are formed so the cross cuts are located proximal to the groove formed in the single said flute.

9. The bur of claim 1, wherein said bur head is further formed so that as said flutes extend distally to proximally along said bur head, said flutes extend helically around said bur head.

10. The bur of claim 1, wherein said bur head has a shape consisting of one from the following group consisting of: spherical; acorn head, barrel head, bullet head, egg, pear or drum shaped.

11. The bur of claim 1, wherein formed in the proximal section of said shaft are coupling features that extend inwardly or outwardly from said shaft, said coupling features designed to facilitate the removable engagement of the shaft to a coupling assembly of the surgical handpiece to which said shaft is attached.

12. The bur of claim 1, wherein the single said flute in which the groove is formed is formed with a single groove.

13. A bur for surgical/medical use, said bur including;
a shaft having opposed proximal and distal ends, said shaft having a proximal section adjacent the proximal end shaped for coupling to a surgical handpiece capable of rotating said shaft; and
a head attached to the distal end of said shaft, said head having: a tip that is a most distal end of the head; a longitudinal axis that extends proximally from the tip through said bur head; and a plurality of flutes, each said flute having a rake surface and a clearance surface, the rake surface and clearance surface meeting at a cutting edge, wherein said head is further formed to have:
a first set of a plurality of flutes with clearance surfaces that, adjacent the bur head tip, are located a first acute angle relative to the longitudinal axis of said bur head; and
a second set of a plurality of flutes, wherein the flutes forming the second set of flutes are formed with clearance surfaces that, adjacent the bur head tip, are located a second acute angle relative to the longitudinal axis of said bur head, the second acute angle being less than the first acute angle so that in a common plane perpendicular to the longitudinal axis of the bur head, the cutting edges of the flutes of the first set of flutes project radially outwardly from the cutting edge of the flutes of the second set of flutes and
wherein, a single one and only one of said flutes that collectively form the first set of flutes and the second set of flutes is formed with a single groove, the single said flute being formed in one of the flutes forming the first plurality of flutes and said flute being formed so that: the groove extends from the rake surface to the clearance surface of said flute; and the groove is spaced proximally from the tip of said head so as to separate the cutting edge of said flute into a distal section located distal to the groove and a proximal section located proximal from the groove.

14. The bur of claim 13, wherein said bur head is further formed so that the first set of flutes includes only two said flutes and said flutes forming the first set of flutes are symmetric to each other relative to the bur head tip.

15. The bur head of claim 13, wherein said bur head is further formed so that a plurality of flutes from the second set of flutes are located between each pair of arcuately adjacent flutes from the first set of flutes.

16. The bur of claim 13, wherein said bur head is further formed so that:
the first set of flutes includes only two said flutes and said flutes forming the first set of flutes are symmetric to each other relative to the bur head tip;
there are a plurality of second flutes located in each space located between the two said flutes forming the first pair of flutes.

17. The bur of claim 13, wherein the groove is formed in said flute so as to have a longitudinal axis that is at an angle of between 80° and 100° of the portion of the flute cutting edge interrupted by the groove.

18. The bur of claim 13, wherein at least one said flute is formed to have a cross cut that extends across said flute, the cross cut being located along said bur head so as to be located proximal to the groove formed in the single said flute.

19. The bur of claim 13, wherein a plurality of said flutes, including the single said flute formed with the groove, are formed so as to each have a cross cut and said flutes are formed so the cross cuts are located proximal to the groove formed in the single said flute.

20. The bur of claim 13, wherein said bur head is further formed so that as said flutes extend distally to proximally along said bur head, said flutes extend helically around said bur head.

21. The bur of claim 13, wherein said bur head is further formed so that as said flutes extend distally to proximally along said bur head, said flutes extend helically around said bur head, the helix having a helix angle that varies along said flutes and so that the rake surfaces of the flutes have rake angles along said flutes that vary along said flutes.

22. The bur of claim 13, wherein said bur head has a shape consisting of one from the following group consisting of: spherical; acorn head, barrel head, bullet head, egg, pear or drum shaped.

23. The bur of claim 13, wherein formed in the proximal section of said shaft are coupling features that extend inwardly or outwardly from said shaft, said coupling features designed to facilitate the removable engagement of the shaft to a coupling assembly of the surgical handpiece to which the shaft is attached.

* * * * *